United States Patent [19]

Berg et al.

[11] Patent Number: 4,488,937

[45] Date of Patent: Dec. 18, 1984

[54] SEPARATION OF M-XYLENE FROM O-XYLENE BY EXTRACTIVE DISTILLATION

[76] Inventors: Lloyd Berg, 1314 S. Third Ave.; An-I Yeh, 1014 S. Sixth Ave., both of Bozeman, Mont. 59715

[21] Appl. No.: 599,277

[22] Filed: Apr. 11, 1984

[51] Int. Cl.³ .......................... B01D 3/40; C07C 7/08
[52] U.S. Cl. ........................ 203/51; 203/58; 203/60; 203/63; 203/69; 203/56; 203/57; 203/61; 203/62; 203/64; 203/65; 585/805
[58] Field of Search ............ 203/50, 51, 52, 56, 203/57, 59, 60, 62, 63, 64, 66, 67, 68, 69, 58, 61, 65; 585/805, 857, 862, 866

[56] References Cited

U.S. PATENT DOCUMENTS

| 2,456,561 | 12/1948 | Lake et al. | 203/60 |
| 2,721,170 | 10/1955 | Johnson | 203/60 |
| 2,738,372 | 3/1956 | Talbot | 585/805 |
| 2,880,253 | 3/1959 | Jezl et al. | 585/805 |
| 2,957,811 | 10/1960 | Geiser | 585/862 |
| 3,116,224 | 12/1963 | Bailey, Jr. | 203/57 |
| 4,024,028 | 5/1977 | Haskell | 585/857 |

FOREIGN PATENT DOCUMENTS

| 0639564 | 4/1962 | Canada | 585/805 |
| 0659726 | 3/1963 | Canada | 585/805 |
| 0625167 | 5/1961 | Italy | 203/58 |

Primary Examiner—Wilbur Bascomb
Assistant Examiner—Virginia Manoharan

[57] ABSTRACT m-Xylene is difficult to separate from o-xylene by conventional rectification or distillation because of the close proximity of their boiling points. m-Xylene can be readily separated from o-xylene by using extractive distillation in which the extractive agent is ethyl-2-hydroxybenzoate; propoxypropanol puls 1,4-butanediol; sulfolane plus dimethylsulfoxide plus ethyl benzoate.

2 Claims, No Drawings

SEPARATION OF M-XYLENE FROM O-XYLENE BY EXTRACTIVE DISTILLATION

This application is related to application Ser. No. 599,278 filed Apr. 11, 1984 by Lloyd Berg and An-I Yeh which also is directed to the separation of xylenes by extractive distillation using other agents.

FIELD OF THE INVENTION

This invention relates to a method for separating m-xylene from o-xylene using individual or mixtures of two or more organic compounds as extractive agents in extractive distillation.

DESCRIPTION OF THE PRIOR ART

Extractive distillation is the method of separating close boiling compounds by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The operation to separate benzene from close boiling non-aromatic hydrocarbons has been well described by Butler, U.S. Pat. No. 3,114,783. He suggests a large number of pure compounds including alcohols, glycol ethers and sulfolanes to separate both benzene and toluene. No information is given here on the relative volatility and thus relative performance of these compounds as extractive distillation agents. Atlani et al, French Pat. No. 2,335,584, July 15, 1977 describes the use of several cyanamide derivatives as extractive agents for separating aromatics including benzene from naphthenes and dienes Cooper, U.S. Pat. No. 2,655,467 employs molten phthalic anhydride as the extractive distillation agent to separate aromatics including benzene from non-aromatic hydrocarbons. P. Mikitinko, G. Cohen and L. Asselinieau, German Pat. No. 2,313,603, Sept, 27, 1973, separated both benzene and toluene from non-aromatic hydrocarbons using dimethyl formamide and dimethyl acetamide. P. Mikitinko and L. Asselinieau in German Pat. No. 2,809,985, Sept. 14, 1978, use these same reagents with water added to bring the non-aromatic hydrocarbons off overhead as a two-phase azeotrope and thus lower the boiling point. K. Eisenlohr and H. Mueller in German Pat. No. 2,263,344, Dec. 23, 1972 reported on an improved equipment arrangement to separate both benzene and toluene from non-aromatic hydrocarbons by extractive distillation. G. Preusser, M. Schulze, K. Richter and W. Heuwels in German Pat. No. 1,960,857, Dec. 4, 1969 described the use of morpholine and some of its derivatives for this separation. Improved equipment for this separation was presented by E. Mueller and K. P. John in German Pat. No. 1,808,758, Nov. 14, 1968. L. Berg, U.S. Pat. No. 4,363,704 described the separation of toluene from close boiling non-aromatic hydrocarbons. The separation of isomers by extractive distillation has received considerably less attention. L. Berg, U.S. Pat. Nos. 4,292,142 and 4,299,668 described the use of chloro compounds and oxygenated compounds to separate ethylbenzene from p-xylene and m-xylene. Prior to this invention, nothing has been reported in the separation by extractive distillation of one xylene from another xylene.

The advantage of using extractive distillation in this separation can be seen from Table 1 below.

TABLE 1

Theoretical and Actual Plates Required vs. Relative Volatility for m-Xylene - o-Xylene Separation.

| Relative Volatility | Theoretical Plates Required at Total Reflux, 95% Purity | Actual Plates Required, 75% Eff. |
|---|---|---|
| 1.12 | 52 | 70 |
| 1.20 | 33 | 44 |
| 1.25 | 27 | 36 |
| 1.30 | 23 | 31 |
| 1.35 | 20 | 27 |
| 1.40 | 18 | 24 |

The relative volatility of m-xylene to o-xylene is about 1.12. To separate these two by conventional rectification requires a minimum of 52 theoretical plates. This however is at total reflux. At a specific reflux, it will be more. The theoretical plates have to be converted to actual plates. Plate efficiencies of 75% are commonly employed and this is the basis of the actual plate listing in Table 1. Thus more than 70 actual plates are required, clearly a difficult separation. Several extractive distillation agents that we have discovered push the relative volatility as high as 1.4 and Table 1 shows that they will reduce the actual plate requirement to something close to 24 plates. Converting the total reflux to an actual reflux will increase the plate requirement somewhat but still make for a very attractive separation.

Extractive distillation typically requires the addition of an equal amount to twice as much extractive agent as close boiling compounds on each plate of the rectification column. The extractive distillation agent should be heated to about the same temperature as the plate into which it is introduced. Thus extractive distillation imposes an additional heat requirement on the column as well as somewhat larger plates for the same product output. To be economically attractive, the extractive distillation system must save more in the reduction of the number of theoretical plates and the size of the column than it adds in the cost of larger plates and the additional heat requirement. This will vary depending on the difficulty of the separation and the cost of heat. We found that in the separation of m-xylene from o-xylene, the extractive agent should increase the relative volatility to about 1.3 to make the process economically attractive under the equipment and heat costs in effect at the time of our investigation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference.

The xylenes are major precursors to many processes for making plastics and dyes. In these uses it is absolutely essential that the xylenes be very pure. It is the presence of impurities that make them poor polymerizing agents as a plastic or render them inconsistent as dye intermediates. The xylenes of commerce originate either from coal tar or from petroleum, usually via the hydroforming of the corresponding naphthenes and thus are always found as mixtures of isomers.

OBJECTIVE OF THE INVENTION

The object of this invention is to provide a process or method of extractive distillation that will enhance the apparent relative volatility of m-xylene to o-xylene in their separation in a rectification column. It is a particular object of this invention to identify suitable combinations of organic compounds which will increase the apparent relative volatility of m-xylene to o-xylene to values higher than 1.3. It is a further object of this invention to identify mixtures of organic compounds which, in addition to the above constraints, are stable, can be separated from o-xylene by rectification with relatively few actual plates and can be recycled to the extractive distillation column and reused with little decomposition.

SUMMARY OF THE INVENTION

The objects of this invention are provided by a process for the separation on m-xylene from o-xylene using sulfolane, benzoates, dimethylformamide, propoxypropanol and/or oxygenated, nitrogenous or sulfur containing organic compounds as the agent in extractive distillation.

DETAILED DESCRIPTION OF THE INVENTION

We have discovered that sulfolane, benzoates, dimethylformamide and propoxypropanol, singly but principally in mixtures will enhance the relative volatility of m-xylene or o-xylene. m-Xylene (b.p.=139.2° C.) and o-xylene (b.p.=144.5° C.) have a relative volatility of 1.12. We have discovered a number of extractive distillation agents which will enhance the relative volatility of these two to the 1.3 to 1.4 range.

Table 2 lists a number of oxygenated, nitrogenous and sulfur containing compounds which when mixed with sulfolane are effective extractive distillation agents. Table 3 shows a number of organic compounds which when mixed with various benzoates, are excellent extractive distillation agents for this separation. Table 4 shows that dimethylformamide (DMFA) either alone or mixed with certain organic compounds, is an effective agent. Table 5 shows that propoxypropanol mixed with certain organic compounds, is an effective agent in this separation.

All of the systems in Tables 2, 3, 4 and 5 possess a relative volatility of 1.3 or greater. The relative volatilities shown in Table 2, 3, 4 and 5 are the average of two runs, one at one part of extractive agent per part of xylene mixture and the other at 6/5 parts of extractive agent per part of xylene mixture. We have found that this is the preferred ratio of extractive distillation agent to xylenes in this separation. The amount of each compound in the binarys and ternarys was approximately equal to each other. The exact ratio does not appear to be critical. Likewise the relative volatilities shown in Tables 2, 3, 4 and 5 do not change appreciably when the ratio of m-xylene to o-xylene is varied. The data presented in Tables 2, 3, 4 and 5 were obtained in a glass vapor-liquid equilibrium still of the Othmer design.

Several of the agents listed in Table 2–5 and whose relative volatilities had been determined in the vapor-liquid equilibrium still, were then evaluated in a glass perforated plate rectification column possessing 4.5 theoretical plates and a glass column packed with Berl saddles possessing 2.4 theoretical plates.

TABLE 2

Relative Volatilities of m-Xylene - o-Xylene With Mixtures Containing Sulfolane.

| Extractive Distillation Agent | Relative Volatility |
| --- | --- |
| Sulfolane | 1.30 |
| Sulfolane, Diethylene glycol | 1.32 |
| Sulfolane, Dibutyl phthalate | 1.32 |
| Sulfolane, Adiponitrile, Acetophenone | 1.34 |
| Sulfolane, Adiponitrile, Nitrobenzene | 1.36 |
| Sulfolane, Adiponitrile, Maleic anhydride | 1.32 |
| Sulfolane, Adiponitrile, 1,4-Butanediol | 1.30 |
| Sulfolane, Adiponitrile, Ethyl benzoate | 1.36 |
| Sulfolane, DMSO, Benzyl alcohol | 1.32 |
| Sulfolane, DMSO, Dibutyl phthalate | 1.34 |
| Sulfolane, DMSO, Acetophenone | 1.34 |
| Sulfolane, DMSO, Nitrobenzene | 1.34 |
| Sulfolane, DMSO, Benzyl cyanide | 1.33 |
| Sulfolane, DMSO, Adiponitrile | 1.32 |
| Sulfolane, DMSO, Diethylene glycol | 1.33 |
| Sulfolane, DMSO, Isophorone | 1.31 |
| Sulfolane, DMSO, Benzoic acid | 1.30 |
| Sulfolane, DMSO, Ethyl benzoate | 1.34 |
| Sulfolane, DMSO, Methyl benzoate | 1.30 |
| Sulfolane, DMSO, Phenyl acetic acid | 1.31 |
| Sulfolane, DMSO, Adiponitrile, Ethyl benzoate | 1.31 |
| Sulfolane, Ethyl benzoate, Benzyl cyanide | 1.31 |
| Sulfolane, Maleic anhydride, Ethyl benzoate | 1.31 |
| Sulfolane, Maleic anhydride, Nitrobenzene | 1.34 |
| Sulfolane, Maleic anhydride, Ethylene carbonate | 1.35 |
| Sulfolane, Maleic anhydride, Propylene carbonate | 1.31 |
| Sulfolane, Maleic anhydride, Dimethylformamide | 1.36 |
| Sulfolane, Phthalic anhydride, DMSO | 1.30 |
| Sulfolane, Phthalic anhydride, Ethylene carbonate | 1.30 |
| Sulfolane, Phthalic anhydride, Propylene carbonate | 1.32 |
| Sulfolane, Phthalic anhydride, Adiponitrile | 1.31 |
| Sulfolane, Ethyl benzoate, Diethylene glycol | 1.31 |
| Sulfolane, Ethylene carbonate | 1.34 |
| Sulfolane, Adiponitrile, Ethylene carbonate | 1.33 |
| Sulfolane, Adiponitrile, Propylene carbonate | 1.30 |

TABLE 3

Relative Volatilities of m-Xylene - o-Xylene With Mixtures Containing Benzoates.

| Extractive Distillation Agent | Relative Volatility |
| --- | --- |
| Methyl benzoate, Butyl benzoate | 1.33 |
| Methyl benzoate, Ethyl benzoate | 1.34 |
| Methyl benzoate, Diisodecyl phthalate | 1.30 |
| Methyl benzoate, Diphenyl isophthalate | 1.35 |

TABLE 3-continued

Relative Volatilities of m-Xylene - o-Xylene With Mixtures Containing Benzoates.

| Extractive Distillation Agent | Relative Volatility |
|---|---|
| Methyl benzoate, DMSO, Butyl benzoate | 1.38 |
| Methyl benzoate, DMSO, Ethyl benzoate | 1.33 |
| Ethyl benzoate, Diphenyl terephthalate | 1.31 |
| Ethyl benzoate, Ethylene glycol phenyl ether | 1.33 |
| Ethyl benzoate, Dimethyl phthalate | 1.30 |
| Ethyl benzoate, DMSO, Butyl benzoate | 1.31 |
| Ethyl benzoate, Ethylene glycol phenyl ether, Methyl salicylate | 1.31 |
| Ethyl benzoate, Ethylene glycol phenyl ether, Benzyl alcohol | 1.30 |
| Ethyl benzoate, Butyl benzoate, Benzyl butyl phthalate | 1.31 |
| Butyl benzoate | 1.33 |
| Butyl benzoate, Diphenyl isophthalate | 1.35 |
| Benzyl benzoate, Benzyl butyl phthalate | 1.32 |
| Benzyl benzoate, Ethyl-4-hydroxybenzoate | 1.33 |
| Benzyl benzoate, Methyl-4-hydroxybenzoate | 1.31 |
| Benzyl benzoate, Ethyl-2-hydroxybenzoate | 1.39 |
| Benzyl benzoate, Methyl-2-hydroxybenzoate | 1.38 |
| Benzyl benzoate, Butyl benzoate | 1.31 |
| Benzyl benzoate, Benzoic acid | 1.32 |
| Benzyl benzoate, DMSO, Methyl-2-hydroxybenzoate | 1.42 |
| Benzyl benzoate, DMSO, Ethyl-2-hydroxybenzoate | 1.33 |
| Benzyl benzoate, DMSO, Methyl benzoate | 1.34 |
| Benzyl benzoate, DMSO, Ethyl benzoate | 1.35 |
| Benzyl benzoate, DMSO, Butyl benzoate | 1.34 |
| Benzyl benzoate, DMSO, Benzoic acid | 1.32 |
| Methyl-2-hydroxybenzoate | 1.39 |
| Methyl-2-hydroxybenzoate, Diisononyl phthalate Butyl benzoate | 1.32 |
| Methyl-2-hydroxybenzoate, Benzyl benzoate | 1.37 |
| Methyl-2-hydroxybenzoate, Methyl benzoate | 1.30 |
| Methyl-2-hydroxybenzoate, DMSO, Butyl benzoate | 1.34 |
| Methyl-2-hydroxybenzoate, DMSO, Ethyl benzoate | 1.33 |
| Methyl-2-hydroxybenzoate, DMSO, Methyl benzoate | 1.37 |
| Butyl-4-hydroxybenzoate, bis-Phenol A | 1.34 |
| Ethyl-2-hydroxybenzoate | 1.34 |
| Ethyl-2-hydroxybenzoate, Methyl benzoate | 1.35 |
| Ethyl-2-hydroxybenzoate, Butyl benzoate | 1.33 |
| Ethyl-2-hydroxybenzoate, Methyl-2-hydroxybenzoate | 1.36 |
| Ethyl-2-hydroxybenzoate, Ethyl benzoate | 1.30 |
| Ethyl-2-hydroxybenzoate, DMSO, Methyl benzoate | 1.37 |
| Ethyl-2-hydroxybenzoate, DMSO, Ethyl benzoate | 1.32 |
| Ethyl-2-hydroxybenzoate, DMSO, Butyl benzoate | 1.35 |
| Ethyl-2-hydroxybenzoate, DMSO, Methyl-2-hydroxybenzoate | 1.31 |
| Ethyl-2-hydroxybenzoate, Diphenyl isophthalate | 1.32 |
| Diethylene glycol dibenzoate | 1.30 |
| Diethylene glycol dibenzoate, Methyl benzoate | 1.34 |
| Diethylene glycol dibenzoate, Ethyl benzoate | 1.36 |
| Diethylene glycol dibenzoate, Benzyl benzoate | 1.35 |
| Diethylene glycol dibenzoate, Butyl benzoate | 1.30 |
| Diethylene glycol dibenzoate, Methyl-2-hydroxybenzoate | 1.31 |
| Diethylene glycol dibenzoate, Ethyl-2-hydroxybenzoate | 1.39 |
| Dipropylene glycol dibenzoate (DPGDB) | 1.33 |
| DPGDB, Diphenyl isophthalate | 1.34 |
| DPGDB, Ethyl benzoate | 1.39 |
| DPGDB, Benzyl benzoate | 1.30 |
| DPGDB, Methyl benzoate | 1.31 |
| DPGDB, Ethyl-2-hydroxybenzoate | 1.30 |
| DPGDB, Diethylene glycol dibenzoate | 1.32 |
| DPGDB, Methyl-2-hydroxybenzoate | 1.40 |
| DPGDB, DMSO | 1.38 |
| DPGDB, DMSO, Benzyl benzoate | 1.33 |
| DPGDB, DMSO, Methyl benzoate | 1.39 |
| DPGDB, DMSO, Methyl-2-hydroxybenzoate | 1.40 |
| DPGDB, DMSO, Ethyl-2-hydroxybenzoate | 1.36 |
| DPGDB, DMSO, Butyl benzoate | 1.31 |
| DPGDB, DMSO, Butyl benzyl phthalate | 1.33 |
| DPGDB, DMSO, Methyl benzoate, Diphenyl isophthalate | 1.39 |
| DPGDB, DMSO, Butyl-4-hydroxybenzoate - 4-hydroxybenzoate | 1.30 |
| DPGDB, DMSO, Ethyl benzoate, Adiponitrile | 1.32 |
| DPGDB, Diethylene glycol dibenzoate, Methyl-2-hydroxybenzoate | 1.35 |
| DPGDB, Diethylene glycol dibenzoate, Methyl-2-hydroxybenzoate, DMSO | 1.33 |
| DPGDB, Diethylene glycol dibenzoate, Ethyl-2-hydroxybenzoate | 1.31 |
| DPGDB, Diethylene glycol dibenzoate, Ethyl-2-hydroxybenzoate, DMSO | 1.34 |
| DPGDB, Diphenyl isophthalate, Methyl-2-hydroxybenzoate | 1.35 |
| DPGDB, Diphenyl isophthalate, Ethyl-2-hydroxybenzoate | 1.37 |

TABLE 4

Relative Volatilities of m-Xylene - o-Xylene With Mixtures Containing Dimethylformamide (DMFA).

| Extractive Distillation Agent | Relative Volatility |
| --- | --- |
| Dimethylformamide (DMFA) | 1.33 |
| Dimethylformamide (DMFA), Ethylene glycol | 1.34 |
| Dimethylformamide (DMFA), 1,4-Butanediol, | 1.32 |
| Dimethylformamide (DMFA), 1,5-Pentanediol | 1.31 |
| Dimethylformamide (DMFA), Diethylene glycol | 1.32 |
| Dimethylformamide (DMFA), Triethylene glycol | 1.32 |
| Dimethylformamide (DMFA), Ethylene glycol phenyl ether | |
| Dimethylformamide (DMFA), Adiponitrile, 1,4-Butanediol | 1.35 |
| Dimethylformamide (DMFA), Adiponitrile, Dihexyl phthalate | 1.34 |
| Dimethylformamide (DMFA), Hydroquinone, m-Cresol | 1.33 |
| Dimethylformamide (DMFA), Hydroquinone, p-Cresol | 1.33 |

TABLE 5

Relative Volatilities of Mixtures Containing Propoxypropanol.

| Extractive Distillation Agent | Relative Volatility |
| --- | --- |
| Propoxypropanol, 1,4-Butanediol | 1.35 |
| Propoxypropanol, propylene glycol | 1.35 |
| Propoxypropanol, 1,5-Pentanediol | 1.31 |
| Propoxypropanol, Hexylene glycol | 1.35 |
| Propoxypropanol, Diethylene glycol | 1.38 |

TABLE 6

Data From Runs Made In Rectification Columns.

| Agent | Column Type | Wt. % of m-Xylene Overhead | Wt. % of m-Xylene Bottoms | Relative Volatility |
| --- | --- | --- | --- | --- |
| Methyl benzoate | Perforated plate | 51.2 | 31.1 | 1.21 |
| Ethyl benzoate | Perforated plate | 50.0 | 30.6 | 1.20 |
| Benzyl benzoate | Perforated plate | 50.7 | 27.8 | 1.24 |
| Methyl benzoate | Packed | 40.7 | 28.4 | 1.26 |
| Ethyl benzoate | Packed | 41.6 | 28.1 | 1.29 |

Notes:
The feed mixture was 150 gr. m-xylene and 350 gr. o-xylene. The agent was added at a rate of 20 ml/min. and 65° C. Total reflux was 5-10 ml/min.

THE USEFULNESS OF THE INVENTION

The usefulness or utility of this invention can be demonstrated by referring to the data presented in Table 2, 3, 4, 5 and 6. When m-xylene is being separated from o-xylene, relative volatility 1.12, by rectification in 95% purity, Table 1 shows that about 70 actual plates are required. Table 3 shows that a mixture of methyl benzoate and diphenyl isophthalate changes the relative volatility to 1.35 and referring to Table 1, this requires only 27 actual plates. Table 3 shows that when the extractive distillation agent is a mixture of dipropylene glycol dibenzoate and methyl-2-hydroxybenzoate, the relative volatility becomes 1.40 and from Table 1, only 24 actual plates will be required to separate m-xylene from o-xylene in 95% purity.

WORKING EXAMPLES

Example 1

A mixture comprising 50 grams of m-xylene and 50 grams of o-xylene was charged to an Othmer type vapor-liquid equilibrium still and the mixture refluxed for twelve hours. Samples of vapor and liquid were removed and analysed by gas chromatography. The vapor contained 51.8% m-xylene, 48.2% o-xylene, the liquid 49% m-xylene, 51% o-xylene. This indicates a relative volatility of m-xylene to o-xylene of 1.12.

Example 2

A mixture comprising 25 grams of m-xylene, 25 grams of o-xylene and 50 grams of ethyl-2-hydroxybenzoate was charged to the vapor-liquid equilibrium still used in Example 1 and refluxed for eleven hours. Analyses indicated a vapor composition of 56.3% m-xylene, 43.7% m-xylene and a liquid composition of 48.5% m-xylene, 51.5% o-xylene. This indicates a relative volatility of 1.37. Ten grams of ethyl-2-hydroxybenzoate was added and refluxing continued for nine hours. Analyses gave a vapor composition of 55% m-xylene, 45% o-xylene, a liquid composition of 48.1% m-xylene, 51.9% o-xylene which is a relative volatility of 1.32.

Example 3

A mixture comprising 25 grams of m-xylene, 25 grams of o-xylene, 25 grams of propoxypropanol and 25 grams of 1,4-butanediol was charged to the vapor-liquid equilibrium still and refluxed for thirteen hours. Analyses indicated a vapor composition of 47.9% m-xylene, 52.1% o-xylene and a liquid composition of 40% m-xylene, 60% o-xylene. This indicates a relative volatility of 1.38. Five grams each of propoxypropanol and 1,4-butanediol was added and refluxing continued for another eleven hours. Analyses indicated a vapor composition of 54% m-xylene, 46% o-xylene, a liquid composition of 47% m-xylene, 53% o-xylene which is a relative volatility of 1.32.

Example 4

A mixture comprising 25 grams of m-xylene, 25 grams of o-xylene, 17 grams of sulfolane, 17 grams of DMSO and 17 grams of ethyl benzoate was charged to the vapor-liquid equilibrium still and refluxed for fifteen hours. Analyses indicated a vapor composition of 54.8% m-xylene, 45.2% o-xylene and a liquid composition of 47.3% m-xylene, 52.7% o-xylene. This indicates a relative volatility of 1.35. Three grams each of sulfolane, DMSO and ethyl benzoate was added and refluxing continued for another eleven hours. Analyses indicated a vapor composition of 54% m-xylene, 46% o-xylene, a liquid composition of 46.7% m-xylene, 53.3% o-xylene which is a relative volatility of 1.34.

These examples serve to show in detail how the data presented in Tables 2, 3, 4 and 5 were obtained. Each of the solvent combinations reported there was determined in this manner.

Example 5

A column consisting of one five plate section of 1½" diameter glass perforated plates equipped with a vacuum jacket was employed. The column was fitted with a Corad head constant reflux ratio distilling head. Between the Corad head and the top of the column, a feed line from a constant flow bellows pump was introduced. The column had been calibrated with a test mixture of ethylbenzene and p-xylene, which mixture possesses a relative volatility of 1.06. The column was calibrated as 4.5 theoretical plates at total reflux. A run was made with a charge comprising approximately 150 grams of m-xylene and 350 grams of o-xylene in the stillpot. The column was operated at total reflux for about an hour and then the pump started at a rate to deliver one part of extractive agent to about two parts of xylenes being boiled up. The extractive agent in this example was benzyl benzoate. The data obtained is presented in Table 6 and shows an overhead analyses of 50.7% m-xylene, a bottoms analysis of 27.8% m-xylene which is a relative volatility of 1.24. Without the extractive agent, it would have been 1.12.

Example 6

A glass column consisting of five inches of Berl saddles as packing and having been calibrated with ethylbenzene-p-xylene to give 2.4 theoretical plates was substituted for the column in Example 5. The extractive distillation agent was ethyl benzoate and operation was similar to Example 5. After 1.5 hours of operation, analyses showed an overhead composition of 41.6% m-xylene, a bottoms composition of 28.1% m-xylene which is a relative volatility of 1.29. Without the extractive agent, it would have been 1.12.

The nature of the present invention having been described and illustrated by examples, what we wish to claim as new and useful and secure by Letters Patent is:

1. A method for recovering m-xylene from a mixture of m-xylene and o-xylene which comprises distilling a mixture of m-xylene and o-xylene in a rectification column in the presence of an effective amount of an extractive agent, recovering essentially pure m-xylene as overhead product and obtaining the extractive agent and o-xylene from the stillpot or reboiler, the extractive agent includes sulfolane.

2. The method of claim 1 in which the extractive agent comprises a mixture of sulfolane and at least on of the group consisting essentially of: adiponitrile, dimethyl-2-hydroxybenzoate, maleic anhydride, phthalic anhydride, dimethylformamide, nitrobenzene, diethylene glycol, dibutyl phthalate, acetophenone, 1,4-butanediol, benzyl alcohol, benzyl, cyanide, methyl benzoate, ethyl benzoate, isophorone, benzoic acid, phenyl acetic acid, ethylene carbonate, propylene carbonate.

* * * * *